(12) United States Patent
Schlesinger et al.

(10) Patent No.: US 7,232,433 B1
(45) Date of Patent: Jun. 19, 2007

(54) MEDICAL DIAGNOSTIC ULTRASOUND CATHETER WITH DIELECTRIC ISOLATION

(75) Inventors: Randall L. Schlesinger, San Mateo, CA (US); Mathew Rahimi, Santa Clara, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/401,632

(22) Filed: Sep. 22, 1999

(51) Int. Cl.
*A61M 25/00* (2006.01)
*A61B 8/00* (2006.01)
*A61B 8/14* (2006.01)

(52) U.S. Cl. ............. 604/527; 604/523; 604/524; 600/437; 600/459

(58) Field of Classification Search ......... 604/20–22, 604/523, 524, 527; 600/443–447, 437, 462, 600/466, 467
See application file for complete search history.

(56) References Cited

U.S. PATENT DOCUMENTS

| | | | |
|---|---|---|---|
| 4,706,670 A | | 11/1987 | Anderson et al. |
| 4,776,086 A | | 10/1988 | Kasevich et al. |
| 4,898,591 A | | 2/1990 | Jang et al. |
| 4,951,677 A | * | 8/1990 | Crowley et al. |
| 5,057,092 A | | 10/1991 | Webster, Jr. |
| 5,176,661 A | | 1/1993 | Evard et al. |
| 5,221,255 A | * | 6/1993 | Mahurkar et al. |
| 5,248,305 A | * | 9/1993 | Zdrahala |
| 5,254,107 A | | 10/1993 | Soltesz |
| 5,328,954 A | * | 7/1994 | Sarangapani |
| 5,368,035 A | | 11/1994 | Hamm et al. |
| 5,398,689 A | * | 3/1995 | Connor et al. .......... 600/459 |
| 5,441,532 A | | 8/1995 | Fenn |
| 5,445,148 A | | 8/1995 | Jaraczewski et al. |
| 5,490,938 A | | 2/1996 | Sawan et al. |
| 5,515,853 A | | 5/1996 | Smith et al. |
| 5,599,294 A | | 2/1997 | Edwards et al. |
| 5,634,466 A | * | 6/1997 | Gruner .......... 600/459 |
| 5,667,499 A | | 9/1997 | Welch et al. |
| 5,669,383 A | | 9/1997 | Johnson |
| 5,676,659 A | | 10/1997 | McGurk |
| 5,683,382 A | | 11/1997 | Leniban et al. |
| 5,683,451 A | | 11/1997 | Lenker et al. |
| 5,685,860 A | | 11/1997 | Chang et al. |
| 5,699,801 A | | 12/1997 | Atalar et al. |
| 5,702,373 A | | 12/1997 | Samson |
| 5,725,513 A | | 3/1998 | Ju et al. |

(Continued)

OTHER PUBLICATIONS

DuPont Product Information, Mylar Polyester Film.

*Primary Examiner*—Catherine S. Williams

(57) ABSTRACT

Medical diagnostic ultrasound catheters are provided with improved materials for dielectric withstand strength. In one aspect, the catheter includes a braid of non-conductive material. The non-conductive braid reduces the capacitive coupling effects and allows smaller catheters or a greater number of conductors. The non-conductive braid provides both compressive and tensile strength to transmit the torque applied to the catheter. The non-conductive braid also allows fusing of components while decreasing the risk of defective manufacture. In another aspect, a dielectric film, such as a polyester film, is positioned between the transducer and any lens or window. The dielectric film allows thinner window lenses to be used, allowing smaller catheters or larger transducers. The dielectric film may also increase the sensitivity of the transducer to acoustic energy. The dielectric film prevents the lens or window material from filling kerfs in the transducer, which may eliminate the need for filling the kerfs of the transducer.

31 Claims, 1 Drawing Sheet

U.S. PATENT DOCUMENTS

| | | |
|---|---|---|
| 5,728,063 A | 3/1998 | Preissman et al. |
| 5,741,325 A | 4/1998 | Chaikof et al. |
| 5,762,067 A * | 6/1998 | Dunham et al. ............ 600/462 |
| 5,769,796 A | 6/1998 | Palermo et al. |
| 5,817,325 A | 10/1998 | Sawan et al. |
| 5,827,201 A | 10/1998 | Samson et al. |
| 5,849,311 A | 12/1998 | Sawan et al. |
| 5,853,422 A | 12/1998 | Huebach et al. |
| 5,857,974 A * | 1/1999 | Eberle et al. |
| 5,899,892 A * | 5/1999 | Mortier et al. |
| 5,954,654 A | 9/1999 | Eaton et al. |
| 5,971,925 A * | 10/1999 | Hossack et al. ............ 600/443 |
| 6,171,295 B1 * | 1/2001 | Garabedian et al. ........ 604/524 |
| 6,325,790 B1 * | 12/2001 | Trotta ........................ 604/523 |

* cited by examiner

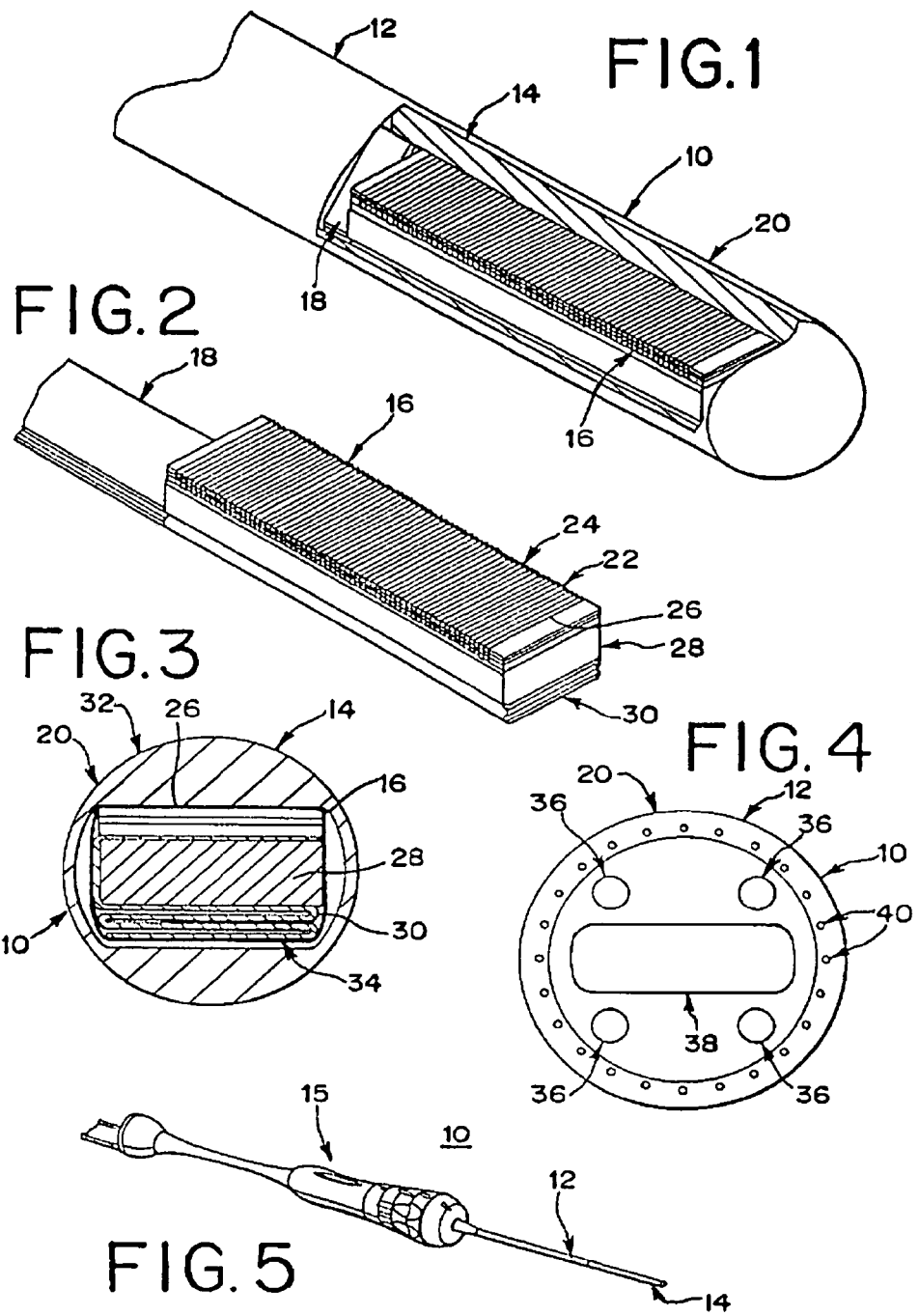

MEDICAL DIAGNOSTIC ULTRASOUND CATHETER WITH DIELECTRIC ISOLATION

BACKGROUND

This invention relates to medical diagnostic ultrasound catheters. In particular, different materials for constructing medical diagnostic ultrasound catheters provide improvements in dielectric isolation.

Catheters for use with ultrasound systems include transducers for converting electrical energy to acoustic energy and vice versa. Images of a region of a patient adjacent to the transducer are generated. In order to provide accurate imaging, a window or lens is integrated with the catheter adjacent to the transducer. The remainder of the exterior of the catheter generally comprises polyurethane or other biologically acceptable material. In order to provide torque transmission and flexibility, an internal metal braid is provided.

For safe inter-cardiac use of a catheter, the catheter must dielectrically withstand 3,000 volts for 60 seconds between the external surface of the catheter and any internal conductors or electrically active components when internal voltages are greater than 50 volts. Additionally, any leakage current must be less than 50 microamps when 264 volts are applied to the internal conductors. Alternating current capacitive coupling causes a voltage to be applied to the metal braid when voltage is applied to the internal conductors. The capacitive coupling decreases the dielectric withstand strength of the catheter and requires a thicker coating material, such as the polyurethane. However, smaller catheters are generally desired.

Components are often thermally fused with the shaft of the catheter. Since the fusing is thermal, portions of the metal braid, such as exposed end wires, may migrate towards the outside surface of the catheter. A fused catheter more likely will not pass the safety requirements due to migration of the metal braid, resulting in wasted production. The metal braid may migrate to the surface, allowing potential corrosion.

These safety requirements apply to the entire catheter, including the tip area with the transducer. The adjacent lens or window material must satisfy the safety requirements. In order to provide the proper dielectric withstand, the thickness of the lens or window material is increased. However, the required thickness may be considerable. The greater the thickness, the larger the catheter or the less room for transducer components, such as desired additional transducer elements and associated conductors.

To avoid increasing the thickness of the shaft or lens of the catheter, each conductor may be isolated with a transformer. Such isolation requires a different dielectric withstand standard for safety, such as a 300 volt standard. For ultrasound imaging with high resolution, multiple conductors are used, such as 64 to 128 conductors. Isolating each conductor with a transformer is cost prohibitive.

BRIEF SUMMARY

The present invention is defined by the following claims, and nothing in this section should be taken as a limitation on those claims. By way of introduction, the preferred embodiment described below includes a medical diagnostic ultrasound catheter with materials for improved dielectric withstand strength. In one aspect, the catheter includes a braid of non-conductive material. The non-conductive braid reduces the capacitive coupling effects and allows smaller catheters or a greater number of conductors. The non-conductive braid provides both compressive and tensile strength to transmit the torque applied to the catheter. The non-conductive braid also allows fusing of components while decreasing the risk of defective manufacture.

In another aspect, a dielectric film, such as a polyester film, is positioned between the transducer and any lens or window. The dielectric film allows thinner lenses to be used, allowing smaller catheters or larger transducers. The dielectric film may also increase the sensitivity of the transducer to acoustic energy. The dielectric film prevents the lens material from filling kerfs in the transducer, which may eliminate the need for filling the kerfs of the transducer.

In one embodiment, a medical diagnostic ultrasound catheter for imaging from within a body is provided. The catheter includes a conductor and a shaft surrounding the conductor. A non-conductive braid or insert is connected with the shaft. An ultrasound transducer is connected with the shaft and electrically connects with the conductor.

In other embodiments, a medical diagnostic ultrasound catheter for imaging from within a body includes a dielectric film adjacent to an ultrasound transducer. The ultrasound transducer is connected with a shaft. A lens is adjacent to the ultrasound transducer. In other embodiments, the lens is optional and the dielectric film is between a portion of the shaft and the ultrasound transducer.

Further aspects and advantages of the preferred embodiments are described below in conjunction with the detailed description of the preferred embodiments.

BRIEF DESCRIPTION OF SEVERAL VIEWS OF THE DRAWINGS

FIG. 1 is a perspective view, in partial cutaway, of one preferred embodiment of a portion of a medical diagnostic ultrasound catheter.

FIG. 2 is a perspective view of one preferred embodiment of a transducer and associated conductor for use in the catheter of FIG. 1.

FIG. 3 is a cross-sectional view of one preferred embodiment of a tip portion of the catheter of FIG. 1.

FIG. 4 is a cross-sectional view of one preferred embodiment of a body portion of the catheter of FIG. 1.

FIG. 5 is a perspective view of a preferred embodiment of a medical catheter.

DETAILED DESCRIPTION OF THE PREFERRED EMBODIMENTS

The preferred embodiments of the medical diagnostic ultrasound catheter include one or both of (1) a non-conductive insert for providing torque transmission and (2) a dielectric film extending around at least a portion of a transducer. The non-conductive insert described below prevents or reduces capacitive coupling, allowing for thinner catheter walls. The dielectric film described below allows for less thick lenses adjacent to the transducer while still providing sufficient dielectric withstand for the 3,000 volts safety requirement.

Referring to FIGS. 1 and 5, a medical diagnostic ultrasound catheter is generally shown at 10. The catheter 10 includes a body portion 12 and a tip portion 14. A handle and control portion 15 (FIG. 5) connects with the body portion 12. The tip portion 14 includes a transducer 16 and associated conductors 18. The conductors also pass through the body portion 12. The catheter 10, including the body portion 12 and tip portion 14, comprises a shaft 20. While the shaft 20 shown is generally linear, shafts with angles, interruptions and other configurations may be used. In alternative embodiments, the transducer 16 is positioned in other locations different than the tip portion 14 of the catheter 10.

Referring to FIG. 2, the transducer 16 and associated conductors 18 are shown separately from the catheter. The transducer 16 comprises a piezoelectric material. The piezoelectric material is diced into a plurality of transducer elements 22 separated by kerfs 24. In one preferred embodiment, 64 transducer elements 22 are provided. In alternative embodiments more or fewer transducer elements may be used. As shown in FIG. 2, the transducer elements 22 are aligned linearly along a flat surface, but in alternative embodiments one and a half or two dimensional arrays of the elements 22 may be used. In yet other alternative embodiments, some or all of the transducer elements 22 are curved and/or not flat.

The upper surface 26 of the transducer 16 comprises an emitting face. A backing block 28 minimizes the acoustical energy transmitted from the transducer 16 in a direction other than through the emitting face 26.

Each transducer element 22 or a group of transducer elements 22 is electrically connected with a respective conductor 18. In one preferred embodiment, the transducer elements 22 are connected to the conductors 18 through a folded flexible circuit 30. The conductors 18 preferably comprise metalized copper conductors on a polymide substrate (flex circuit). Each circuit has 18 conductors, including ground conductors, where four circuits are stacked to form a bundle.

FIG. 3, shows a cross-section of the tip portion 14 of the catheter 10. The tip portion includes the transducer 16, the backing block 28 and the folded flexible circuit 30. These components are within the shaft 20. The emitting face 26 of the transducer 16 is positioned adjacent a lens section 32 of the shaft 20. The lens section 32 preferably comprises Pebax®, such as Pebax® 3533 manufactured by Elf Autochem, but other polymers, silicones or materials may be used. The lens 32 is shaped to provide no focus or some focus, such as a physical elevation focus for the transducer 16 and is of a material that does not interfere with the transmission of acoustic energy. As used herein, lens includes a window or other structure on the shaft 20 for transmitting acoustic energy between the patient and the transducer 16, including windows that do or do not focus the acoustic waves.

In one preferred embodiment, a dielectric film 34 extends around the circumference and ends of the transducer 16 and associated components, including the backing block 28 and flexible circuit 30. The dielectric film 34 comprises any film providing dielectric insulation. Preferably, a polyester film is used, such as a Mylar® Type C polyester film manufacturing by DuPont. In alternative embodiments, the dielectric film 34 extends only between the emitting face 26 and the shaft 20. In yet other alternative embodiments, the dielectric film is positioned around only part of the transducer 16, backing block 28, flexible circuit 30, and/or conductors 18. The film may be a sheet or a tube.

The dielectric film 34 insulates the outer surface of the catheter 10 from the conductive components associated with the transducer 16. Preferably, the dielectric film 34 is thin enough to not degrade the acoustic signal but thick enough to provide high dielectric withstand strength. For example, the dielectric film 34 may have a thickness of about six microns. A high dielectric withstand strength may allow the thickness of the lens material 34 to be reduced. At six microns, the Mylar® Type C manufactured by DuPont provides a dielectric strength, of 2,000 volts. Other thicknesses can be used, including greater or lesser thicknesses.

In one preferred embodiment, the dielectric film 34 comprises a tape. For example, a backing is peeled off of the dielectric film 34 to expose an adhesive. The adhesive is then used to adhere to the transducer 16 and associated components.

The dielectric film 34 provides dielectric insulation, allowing for a larger transducer 16 or a smaller catheter 10. The dielectric film 34 also prevents the lens or shaft material from entering the kerfs 24 of the transducer 16 during manufacture, avoiding a kerf-filling step.

FIG. 4, shows a cross-sectional view of the body portion 12 of the catheter 10. The body portion 12 includes the shaft 20, lumens 36 for control lines to guide the catheter 10, and a lumen 38 for housing the conductors 18. More or fewer lumens 36 for control lines may be provided. In alternative embodiments, more than one lumen 38 for housing the conductors 18 is provided.

The shaft 20 comprises a polyurethane or other material. Preferably, the shaft 20 comprises Pebax®, such as Pebax® 7233 manufactured by Elf Autochem. The lumens 36 and 38 are bonded or fused at each end of the catheter 10 to the shaft 20 or other components of the catheter 10. In this embodiment, the shaft 20 is hollow. In alternative embodiments, the shaft 20 is not hollow, or the control and/or conductor lumens 36 and/or 38 are fused at other locations within the catheter 10.

The shaft 20 also includes a non-conductive insert 40. The non-conductive insert preferably is configured as a braid embedded within the shaft 20 during manufacture of the shaft 20. The non-conductive insert 40 comprises any non-conductive material, such as plastic, glass, nylon or combinations thereof. In one preferred embodiment, a liquid crystal polymer, Vectron® manufactured by Hoechest-Celanese Acetate, is used. Preferably, the material used comprises a monofilament material. In alternative embodiments, multiple fibers may be used. For example, the non-conductive insert 40 comprises a linear strip, a tube, a spiral winding, a diamond weave or other braid structures using two or more filaments or groups of filaments. Single-stranded or multi-stranded braids may be used. Preferably, a 32 or 64 psi (crossing per inch) diamond weave braid of 2 or 3 mil monofilament is used. The non-conductive insert 40 provides flexibility while transmitting the torque appropriate for use of the catheter 10. For example, the non-conductive insert 40 has a modular of elasticity greater than 4 Mpsi, such as 10 Mpsi and transmits torque along substantially the entire length of the shaft 20.

In one preferred embodiment, the tip portion 14 is thermally fused to the body portion 12 during manufacture. More flexibility may be provided in the catheter 10 if the non-conductive insert 40 does not extend throughout the length of the tip portion 14. The desired rigidity and torque control is provided by embedding the non-conductive insert 40 within the body portion 12.

By using the non-conductive insert 40, the shaft 20 is maintained free of electrically conducting materials. This may reduce the capacitive coupling effect caused by metallic braids. During the thermal fusing operation, portions of the non-conductive insert 40 may migrate closer to an exposed surface of the catheter 10. Such migration does not result in failure of the catheter 10 due to safety requirements. Where the non-conductive insert 40 migrates to the surface, corrosion and harm to the patient is prevented.

While the invention has been described above by reference to various embodiments, it will be understood that many changes and modifications can be made without departing form the scope of the invention. For example, a non-conductive insert may be used without the dielectric film. Likewise the dielectric film may be used without the non-conductive insert. The dielectric film may be used to wrap other electrically conductive parts, such as the conductors.

It is therefore intended that the foregoing detailed description be understood as an illustration of the presently preferred embodiments of the invention, and not as a definition of the invention. It is only the following claims, including all equivalents, that are intended to define this scope of the invention.

What is claimed is:

1. A medical diagnostic ultrasound catheter for imaging from within a body, the catheter comprises:
   a conductor;
   a shaft surrounding at least a portion of the conductor;
   a non-conductive braid connected with the shaft; and
   an ultrasound transducer connected with the shaft and electrically connected with the conductor
   wherein the ultrasound transducer is positioned in a tip portion of the shaft, the tip portion of the shaft being free of the non-conductive braid;
   wherein the shaft is free of electrically conductive material.

2. The catheter of claim 1 wherein the non-conductive braid comprises a braid of mono-filament material.

3. The catheter of claim 1 wherein the non-conductive braid comprises mono-filament nylon material.

4. The catheter of claim 1 wherein the non-conductive braid comprises a material selected from the group consisting of: glass, plastic, nylon and combinations thereof.

5. The catheter of claim 1 wherein the non-conductive braid is embedded within the shaft.

6. The catheter of claim 1 wherein the shaft comprises a tip portion fused to a body portion, the non-conductive braid connected with the body portion.

7. The catheter of claim 1 wherein the non-conductive braid comprises a configuration selected from the group consisting of: spiral, diamond weave and combinations thereof.

8. The catheter of claim 1 further comprising a dielectric film adjacent an emitting surface of the ultrasound transducer.

9. The catheter of claim 1 wherein the non-conductive braid comprises liquid crystal polymer material.

10. A medical diagnostic ultrasound catheter for imaging from within a body, the catheter comprising:
    a catheter shaft;
    an ultrasound transducer connected with the catheter shaft;
    a lens adjacent the ultrasound transducer, the lens having a focus; and
    a dielectric solid film adjacent the ultrasound transducer, the dielectric solid film comprising a polyester film;
    wherein:
    the catheter shaft comprises a tip portion;
    the ultrasound transducer connects with the tip portion; and
    the dielectric film surrounds a circumference of the ultrasound transducer, the circumference being over an emitting surface, a back and at least two sides of the ultrasound transducer.

11. The catheter of claim 10 wherein the dielectric film is positioned between the lens or window and the ultrasound transducer.

12. The catheter of claim 10 wherein the dielectric film-comprises a tape material.

13. The catheter of claim 10 wherein the polyester film comprises Mylar.

14. The catheter of claim 10 wherein the dielectric film comprises a film having a thickness less than 7 microns.

15. The catheter of claim 10 wherein the dielectric film is positioned adjacent an emitting surface of the ultrasound transducer.

16. The catheter of claim 10 further comprising a non-conductive braid connected with the shaft.

17. The catheter of claim 10 wherein the dielectric surrounds the circumference and one end of the ultrasound transducer.

18. The catheter of claim 11 further comprising a flexible circuit connected with the ultrasound transducer, the dielectric film being separate from the flexible circuit, the flexible circuit being between the transducer and the dielectric film.

19. A medical diagnostic ultrasound catheter for imaging from within a body, the catheter comprising:
    a shaft;
    an ultrasound transducer connected within the shaft; and
    a dielectric solid film positioned between a portion of the shaft and the ultrasound transducer, wherein the dielectric surrounds at least a portion of a circumference and one end of the ultrasound transducer, the dielectric solid film having a thickness less than 7 microns.

20. The catheter of claim 19 further comprising a lens adjacent the ultrasound transducer, wherein the dielectric film is positioned between the lens and the ultrasound transducer.

21. The catheter of claim 19 wherein the dielectric film comprises a polyester film.

22. The catheter of claim 19 further comprising a non-conductive braid connected with the shaft.

23. A medical catheter for insertion into a body, the catheter comprising:
    a shaft;
    an electrical conductor connected with a transducer within the shaft; and
    a nonconductive braid connected with the shaft to transmit torque to the shaft wherein the ultrasound transducer is positioned in a tip portion of the shaft, the tip portion of the shaft being fee of the non-conductive braid;
    wherein the shaft is free of electrically conductive material.

24. The catheter of claim 23 wherein the non-conductive braid comprises a braid of mono-filament material.

25. The catheter of claim 23 wherein the non-conductive braid comprises mono-filament liquid crystal polymer material.

26. The catheter of claim 23 wherein the non-conductive braid comprises a material selected from the group consisting of: glass, plastic, nylon and combinations thereof.

27. The catheter of claim 23 wherein the non-conductive braid is embedded within the shaft.

28. The catheter of claim 23 further comprising;
an ultrasound transducer electrically connected to the conductor.

29. The catheter of claim 23 further comprising a control within the shaft.

30. A medical diagnostic ultrasound catheter for imaging from within a body, the catheter comprising:
a catheter shaft;
an ultrasound transducer connected with the catheter shaft;
a dielectric film positioned between a portion of the catheter shaft and the ultrasound transducer; and
a lens adjacent the ultrasound transducer, wherein the dielectric film is positioned between the lens and the ultrasound transducer;
wherein the dielectric film surrounds a circumference of the ultrasound transducer.

31. The catheter of claim 30 further comprising a flexible circuit connected with the ultrasound transducer, the dielectric film being separate from the flexible circuit, the flexible circuit being between the transducer and the dielectric film.

* * * * *